(12) United States Patent
Nur et al.

(10) Patent No.: US 9,365,635 B2
(45) Date of Patent: Jun. 14, 2016

(54) INTRAVENOUS IMMUNOGLOBULIN COMPOSITION

(75) Inventors: Israel Nur, Moshav Timmorim (IL); Liliana Bar, Rehovot (IL); Orgad Laub, Tel-Aviv (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 13/619,011

(22) Filed: Sep. 14, 2012

(65) Prior Publication Data

US 2013/0011388 A1    Jan. 10, 2013

Related U.S. Application Data

(62) Division of application No. 11/201,282, filed on Aug. 11, 2005, now Pat. No. 8,354,249.

(51) Int. Cl.
| | |
|---|---|
| *A61K 38/00* | (2006.01) |
| *C07K 16/08* | (2006.01) |
| *A61K 39/395* | (2006.01) |
| *A61K 39/00* | (2006.01) |

(52) U.S. Cl.
CPC ......... *C07K 16/081* (2013.01); *A61K 39/39591* (2013.01); *A61K 38/00* (2013.01); *A61K 2039/505* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,174,388 A | 11/1979 | McAleer et al. | |
| 4,617,379 A | 10/1986 | Dobkin et al. | |
| 6,468,733 B2 | 10/2002 | Nur et al. | |
| 6,692,739 B1 | 2/2004 | Patti et al. | |
| 2010/0143377 A1* | 6/2010 | Laub et al. ................. | 424/159.1 |

FOREIGN PATENT DOCUMENTS

| | | |
|---|---|---|
| EP | 0128522 | 12/1984 |
| IL | 121900 | 12/2001 |
| WO | 9428934 | 12/1994 |
| WO | 99/18130 | 4/1999 |
| WO | 03/049117 | 12/2003 |

OTHER PUBLICATIONS

Ballow, Intravenous Immunoglobulins: Clinical Experience and Viral Safety, 2002, Journal of the American Pharmaceutical Association, vol. 42, No. 3, pp. 449-459.*
"CDC Smallpox Response Plan and Guidelines" (http://www.bt.cdc.gov/agent/smallpox/response-plan/index.asp#guideb), Draft 3.0—Dated Sep. 21, 2002; Executive Summary, pp. 1-10, Mar. 20, 2003.
Modlin et al "Vaccina (smallpox) vaccine: recommendations of the Advisory Committee on Immunization Practices (ACIP), 2001"
CDC MMWR Recommendations and Reports Jun. 22, 2001; 50(RR-10): 1-25. (2001).
Crance et al "Use of vaccinia immune globulin in the prophlaxis and the treatment of Orthopoxovirus infections" Medecine et maladies infectieuses 34:S46-S47 (2004).
Elder et al., "Carbohydrate Side Chains of Rauscher Leukemia Virus Envelope Glycoproteins Are Not Required to Elicit a Neutralizing Antibody Response" Journal of Virology, 57(1):340-342 (1986).
"European Agreement on the Exchange of Therapeutic Substances of Human Origin" Council of Europe (Jan. 1, 1985) 11 pages.
European Pharmacopoeia "Human Anti-D Immunoglobulin" Monografia 1997:0557 Council of Europe pp. 951-952. (1997).
European Pharmacopoeia 5.0 "Human Hepatitis A Immunoglobulin" Monografia Jan. 2005:0760 Council of Europe pp. 1741 (Jan. 2005).
European Pharmacopoeia 5.0 "Human Rabies Immunoglobulin" Monografia Jan. 2005:0723, Council of Europe pp. 1750-1751 (Jan. 2005).
European Pharmacopoeia 5.0 "Human Tetanus Immunoglobulin" Monografia Jan. 2005:0398 pp. 1751-1175 (Jan. 2005).
European Pharmacopoeia 5.0 "Human Varicella Immunoglobulin" Monografia Jan. 2005:0724, Council of Europe pp. 1752-1753 (Jan. 2005).
Package Insert, "RABIGAM IM" from Natal Bioproducts Institute (Sep. 1996) 3 pages.
Package Insert, "TETAGAM IM" from Natal Bioproducts Institute (Jan. 1996) 3 pages.
Frey et al., "Response to Smallpox Vaccine in Persons Immunized in the Distant Past" JAMA 289(24):3295-3299 (2003).
Haigwood et al. "Passive Immune Globulin Therapy in the SIV/macaque model: early intervention can Alter Disease Profile" Immunol Lett. 51:107-114 (1996).
Henderson et al., "Smallpox as a Biological Weapon" JAMA 281(22):2121-2137 (1999).
Henderson DA Smallpox: Clinical and Epidemiologic Features Emerg. Infect. Dis, 5:537-539 (1999).
Huerta et al., "SWOT Analysis: Strengths, Weaknesses, Opportunities and Threats of the Israeli Smallpox Revaccination Program" Isr Med Assoc J. (2003) 5:42-46 (2003).
Keller et al., 'Passive Immunity in Prevention and Treatment of Infectious Diseases' Clinical Microbiology Reviews 13(4):602-614 (2000).
Mahy et al., "Virology Methods Manual" Academic Press Inc. (SYNOPSIS) (1996).

(Continued)

*Primary Examiner* — Benjamin P Blumel

(57) ABSTRACT

A concentrated, immunoglobulin composition for treating subjects vaccinated against or infected with a pathogenic microorganism, is made by (a) selecting a population of individuals previously vaccinated against antigens associated with the pathogenic microorganism; (b) identifying very high titer individuals by determining the level of specific antibodies immunoreactive with the pathogenic microorganism in the blood of the individuals; (c) combining blood from the very high titer individuals; and (d) purifying and/or concentrating the product of step (c). A concentrated immunoglobulin composition can include specific antibodies immunoreactive with a pathogenic microorganism, wherein the titer of specific antibodies is at least 5 times higher than the average titer of specific antibodies of a population of individuals previously vaccinated against antigens associated with the pathogenic microorganism. The composition has a relatively high protein concentration and a low percentage of protein aggregates. The pathogenic microorganism is preferably smallpox virus or vaccinia virus.

5 Claims, 3 Drawing Sheets

(56) References Cited

OTHER PUBLICATIONS

Quinn et al., Specific, Sensitive, and Quantitative Enzyme-Linked Immunosorbent Assay for Human Immunoglobulin G Antibodies to Anthrax Toxin Protective Antigen Emerg. Infect. Dis., 8(10):1103-1110 (2002).

WHO Smallpox. Weekly Epidemiological Record (2001) 76(44):337-344 (2001).

WHO Recommendations for Production and Control of Smallpox Vaccine, WHO Expert Committee on Biological Standardization 53rd Meeting, Feb. 17-21, 2003. Final Report (2004) WHO Technical report Series 926.

Hopkins et al.,"Safety and Pharmacokinetic Evaluation of Intravenous Vaccinia Immune Globulin in Healthy Volunteers" Clinical Infectious Diseases; Sep. 15, 2004, pp. 759-766; vol. 39, No. 6; ISSN: 1058-4838.

Shimoni et al.,"Treatment of West Nile Virus Encephalitis with Intravenous Immunoglobulin"; Emerging Infectious Diseases, EID; Jul. 2001; p. 759; vol. 7, No. 4; ISSN: 1080-6040.

Nishimura et al. "Determination of a statistically valid neutralization titer in plasma that confers protection against simian-human immunodeficiency virus challenge following passive transfer of high-titered neutralizing antibodies" Journal of Virology 76:2123-2130 (2002).

Summary for Basis of Approval, Feb. 2005, p. 1-18, DynPort Vaccine Company LLC.

Vaccinia Immune Globulin Package Insert, Feb. 2005, p. 1-23, DynPort Vaccine Company LLC.

Cutchins et al.,"The Antibody Response to Smallpox Vaccination As Measured by a Tissue Culture Plaque Method" The Journal of Immunology, 85:275-283 (1960).

http://www.drugs.com/mmx/respigam.html Respiratory Syncytial Virus Immune Globulin Intravenuous (Systemic), downloaded Sep. 30, 2013.

CSL Behring "CytoGam® Cytomegalovirus Immune Globulin Intravenous (Human)" US Package Insert (2007).

\* cited by examiner

INTRAVENOUS IMMUNOGLOBULIN COMPOSITION

FIELD OF THE INVENTION

This invention relates to an intravenous immunoglobulin composition, a method for its preparation, forms of products containing it and therapeutic uses of the composition.

BACKGROUND OF THE INVENTION

Small pox vaccine contains live vaccinia virus, a virus in the orthopoxvirus family and closely related to variola virus, the agent that causes smallpox. Neutralizing antibodies induced by vaccinia vaccine are cross-protective for other Orthopoxviruses. Although the efficacy of vaccinia has never been demonstrated in controlled trials, epidemiologic studies did show an increased level of protection against smallpox which persists for 5 years or less after primary vaccination and substantial but waning immunity that can persist for more than 10 years. Antibody levels after re-vaccination can remain high longer, conferring a greater period of immunity than occurs after primary vaccination alone.

For most people, the vaccinia vaccine is safe and effective. In a non-immune person who is not immuno-suppressed, the expected response to primary vaccination is the development of papule at the site of vaccination 2-5 days after percutaneous administration of vaccinia vaccine. The papule becomes vesicular, then pustular, and reaches its maximum size in 8-10 days. The pustule dries and forms a scab, which separates within 14-21 days after vaccination, leaving a scar.

Most people experience normal, typically mild reactions to the vaccine, like swelling and tenderness of regional lymph nodes, fever, erythematous or urticarial rashes and inadvertent inoculation. Most of these resolve without any treatment.

Some people may experience moderate or severe reactions, which may require medical attention. These complications are rare but occur at least 10 times more often among primary vaccinees than among re-vaccinees and are more frequent among infants and immune-compromised subjects than among older children and adults. In the past, between 14 and 52 subjects per 1 million people vaccinated for the first time experienced potentially life-threatening reactions.

The following complications of vaccinia vaccination require medical attention:

Eczema vaccinatum: Serious skin rashes caused by widespread infection of the skin. Occurs in patients with history of eczema or atopic dermatitis. Lesions begin to appear at distant sites as the virus spreads throughout the body. Usually illness is mild and self-limiting, but can be severe or fatal. The most serious cases among vaccine recipients occur among primary vaccinees and are independent of the activity of the underlying eczema.

Progressive vaccinia (or vaccinia necrosum): Ongoing infection of skin with progressive tissue necrosis. The lesion may progress for months, and secondary lesions can develop elsewhere in the body. The infection is more common in primary vaccinees, immune compromised subjects and in children and is frequently fatal. Occurrence of this complication was influenced by the strain of vaccine virus and was higher in Europe than in the US.

Generalized vaccinia: Is characterized by a diffuse erythematous maculopapular rash indiscriminately scattered over the body. The papules become vesicles and heal over within 15 days. It is thought that generalized vaccinia results from circulatory dissemination of the virus in normal individuals. The irregularity of the lesions and the healthy immune system of affected patients differentiate this disease from erythematous rash and accidental vaccinia.

Post-vaccinal encephalitis: Inflammation of the brain. This is a rare and serious complication and the relationship with the vaccinia virus is still unknown. The encephalitis that occurs in children younger than 2 years is characterized by and incubation period of 6-10 days and is associated with degenerative changes in ganglion cells, perivascular hemorrhage, and generalized hyperemia of the brain. Symptoms are the same as those associated with general encephalitis, including intracranial pressure, myelitis, convulsions and muscular paralysis. A second form of the disease occurs in older children and adults. This is characterized by an incubation period of 11-15 days and is associated with signs of an allergic response with perivascular demyelination. Occurrence of this complication was influenced by the strain of vaccine virus and was higher in Europe than in the US.

Two emerging potentially fatal adverse effects of smallpox vaccination are myopericarditis and ischemic cardiac event. Patients who experience cardiac illness following vaccination report shortness of breath, palpitations, and chest pain. Death from myocardial infarction is a distinct possibility.

Based on past experience, it is estimated that between 1 and 2 people out of every 1 million people vaccinated may die as a result of life-threatening reactions to the vaccine.

Moreover, subjects with weakened immune systems or certain skin conditions are more likely to have severe reactions and are therefore excluded from vaccination with vaccinia, unless they have been exposed to smallpox virus.

Intravenous immunoglobulin (IVIg) is a well known medical product, which consists of a non-specific immunoglobulin solution obtained by combining plasma from a plurality of individuals. Vaccinia Immunoglobulin (VIG) is a solution of immune globulins obtained from plasma collected from subjects who were vaccinated with smallpox vaccine. The solution therefore contains a relatively high titre of anti-vaccinia antibodies.

The preparation of VIG commonly used was an intramuscular (im) product (VIG-IM), and was produced by Baxter Healthcare Corporation in the 1990s. Because it contained a high proportion of aggregated proteins, it was administered solely by the intra-muscular route and could not be used intravenously (iv). Since plasma donors are not selected for high anti-vaccinia antibody levels, the efficacy of VIG treatment is limited and high volumes or multiple injections are needed to reach an effective level.

In general an initial dose of 0.6 ml/kg body weight (about 100 mg/kg=~7 gr/adult treatment) was injected intramuscularly and subsequent administration determined by the course of illness. In severe vaccinia complication such as cases of eczema vaccinatum and progressive vaccinia as much as 1-10 ml/kg were used. These large doses were split into smaller units, and injected intramuscularly at multiple sites spread out over time.

Following the recent threat of bio-terrorist attack, a major effort has been made to produce VIG for intravenous administration (VIG-IV). Preparations of VIG-IV are available (C-VIG, Cangene, Acambis/Baxter; Dyn port). No similar product is currently being developed in the EU. Treatment with VIG-IV requires medical care and therefore has to be administered within a medical center framework.

VIG has been indicated for accidental implantation involving extensive lesions, eczema vaccinatum (EV), generalised vaccinia (GV), and progressive vaccinia (PV). VIG is not recommended for mild instances of accidental implantation, mild or limited generalised vaccinia, erythema multiforme, or encephalitis post-vaccination. VIG can also be useful in treating ocular vaccinia that results from inadvertent implantation. When ocular vaccinia with keratitis is present, consideration of VIG should include the possible increased risk for corneal scarring.

It was suggested that vaccinia immune globulin is also of value in post-exposure prophylaxis of smallpox when given within the first week following exposure, and concurrently with vaccination. Vaccination alone is recommended for those without contraindications to the vaccine, unless greater than one week has elapsed after exposure. At this time, administration of both products, if available, is recommended.

U.S. Pat. No. 4,174,388 (McAleer et al) discloses hepatitis B immune globulin prepared from individuals who exhibit an increase in hepatitis B surface antibody of at least 2,000 PHA units/ml following immunization with hepatitis B surface antigen.

U.S. Pat. No. 4,617,379 (Dobkin et al) discloses the preparation of cytomegalovirus (CMV) hyperimmune serum globulin. The serum globulin is prepared from normal fresh plasma from donors who have not been vaccinated with a CMV vaccine and who have been screened for higher than normal titres of antibody to CMV. Plasma containing high titre antibody to CMV is pooled and fractionated to give the product.

U.S. Pat. No. 6,692,739 (Patti, et al) discloses a method and composition for the passive immunization of patients infected with or susceptible to infection from Staphylococcus bacteria. The composition is prepared from a donor plasma pool obtained by combining individual blood or blood component samples which have higher than normal titres of naturally occurring antibodies to an antigen of the Staphylococcus bacteria. The blood or blood component samples are obtained from a normal, un-vaccinated population. In an alternative embodiment, selected proteins or peptides are administered to a host to induce the expression of desired antibodies, the enhanced high titre serum or plasma pool is recovered from the host, and this pool is administered to a patient in need, optionally after purification and concentration.

WO 03/049117 discloses an intravenously injectable immune globulin having a high titre of antibody to Orthopoxvirus. The immune globulin is prepared by vaccinating a plurality of donors with an Orthopoxvirus vaccine, isolating plasma from each of the donors after a period of time sufficient to allow production of antibodies against the Orthopoxvirus vaccine, and preparing an intravenously injectable immune globulin from the plasma. Also disclosed is a method for treating or preventing an Orthopoxvirus infection, and a method of treating or ameliorating symptoms associated with adverse reaction to Orthopoxvirus vaccination.

SUMMARY OF THE INVENTION

It has now been surprisingly discovered that a certain percentage of a vaccinated population has an exceptionally high titre of antibodies, and that this high titre is stably maintained over time following successive plasmaphereses. This discovery has been applied in the present invention to obtain a novel method and product.

Thus, in one aspect, the present invention provides a method for preparing a concentrated, immunoglobulin composition for treating subjects vaccinated against or infected with a pathogenic microorganism, comprising: (a) selecting a population of individuals previously vaccinated against one or more antigens associated with the pathogenic microorganism; (b) determining the level of specific antibodies immunoreactive with the pathogenic microorganism in a blood or blood component of the individuals to identify very high titre individuals having a very high titre of the specific antibodies; (c) combining blood or blood components comprising immunoglobulins from the very high titre individuals; and (d) purifying and/or concentrating the product of step (c), thereby obtaining a concentrated immunoglobulin composition.

In a preferred embodiment of the invention, the method further comprises the step of aliquoting the concentrated immunoglobulin composition in a low-volume unit dosage form. In a most preferred embodiment, the low-volume unit dosage form comprises a vial or a pre-filled syringe. The use of a low volume significantly decreases risk of side effects, and makes the product easier to administer.

In the present specification, terms will be used at times which should be understood according to the following definitions:

Blood component—a fraction of whole blood comprising immunoglobulins. A preferred blood component is plasma.

Specific antibodies—antibodies having a binding specificity to a particular antigen over other antigens. Although cross-reactivity may exist, the specific antibodies have a significantly higher binding affinity to the specified antigen. An example is antibodies which bind an antigen associated with Vaccinia virus.

Very high titre—high concentration of specific antibodies in an immunoglobulin solution, such as a blood component, generally at least 5 times, and preferably 10 times higher than the average concentration of the specific antibody in a similar immunoglobulin solution in the general population. A very high titre preferably relates to a titre exceeding 5 times and particularly 10 times higher than the average concentration of the specific antibody in a similar immunoglobulin solution obtained from individuals having been previously exposed to an antigen that elicits production of said specific antibody, such as by vaccination. A very high titre may be determined, also, by measuring the ratio of the specific antibody to the general immunoglobulin content in the immunoglobulin solution; such a ratio being 5 times and preferably 10 times higher than the ratio in an immunoglobulin solution with average titre of the specific antibody, and typically being 5 times and desirably 10 times higher than the ratio in an immunoglobulin solution obtained from individuals having been previously exposed to an antigen that elicits production of said specific antibody. In the context of the invention, individuals that have been previously exposed to an antigen that elicits production of said specific antibodies, are typically individuals vaccinated against a pathogenic microorganism, e.g. vaccinia virus.

Very high titre individuals—individuals whose blood contains a very high titre of specific antibodies.

Concentrated immunoglobulin composition—a composition comprising specific antibodies at a very high titre.

OmriUnits/ml—an arbitrary antibody titre measure, calculated using the ELISA immunoassay described below. In the case of Vaccinia virus, 1000 OmriUnits represents an amount of the specific antibodies in 1 ml of pooled plasma obtained from a population of 50 individuals vaccinated with an antigen that elicits production of the specific antibodies in said individuals. It was demonstrated that in the case of the vaccinia virus, 20-40 OmriUnits will neutralize Vaccinia virus in a neutralization assay by about 50%. An example of such a neutralization assay (PRNT50=Plaque Reduction Neutralization Assay 50%) is described below.

Low-volume unit dosage form—a dosage form which may be administered to a patient in a single dispensation, usually by injection. In this form, the patient receives a complete individual treatment in one, brief administration. A preferred volume is less than about 10 ml, more preferably about 5 ml or less, most preferably about 2 ml.

Approximately 10% protein—between 8 to 12% protein concentration, preferably about 10%.

A low aggregate content—less than 3% protein aggregates in a solution, enabling use of the solution for iv administration.

Treating an infection—therapeutic and/or prophylactic treatment of the infection.

In another aspect of the invention, there is provided concentrated immunoglobulin composition comprising specific antibodies immunoreactive with a pathogenic microorganism, characterized in that the titre of specific antibodies of the composition is at least 5 times higher, and preferably 10 times higher, than the average titre of specific antibodies of a population of individuals previously vaccinated against one or more antigens associated with the pathogenic microorganism.

Present immunoglobulin products such as Vaccinia Immunoglobulin (VIG) are made using plasma from non-selected revaccinated donors. That has resulted in a low titer of specific immunoglobulin. Furthermore, due to its low concentration, the prior art product has to be administrated via slow intravenous infusion. In cases of intramuscular injections, the product (of approximately 40 ml volume) has to be administrated at various locations and over several hours.

The concentrated immunoglobulin composition produced in accordance with the invention will be referred to at times, with reference to one preferred embodiment in which the pathogenic microorganism is the vaccinia virus, as HT-VIG (high titre vaccinia immunoglobulin), while the prior art immunoglobulin product will be referred to at times, also with reference to this preferred embodiment, as VIG (vaccinia immunoglobulin). The method of the invention enables selection of very high titer plasma samples resulting in a high potency, low volume product. The very high titer blood or blood components may be repeatedly obtained from each of the high titre individuals.

In a preferred embodiment, the titre of specific antibodies of the concentrated immunoglobulin composition of the invention is at least 5 times higher, more preferably about 10 times higher, than the average titre of specific antibodies of a population of individuals previously vaccinated against one or more antigens associated with the pathogenic microorganism. The concentrated immunoglobulin composition preferably contains at least about 40,000 OmriUnits of the specific antibodies. In another preferred embodiment, the concentrated immunoglobulin composition contains at least approximately 10% protein. The high potency of the concentrated immunoglobulin composition enables it to be administrated at a very low volume (iv or im) and therefore can be used under field conditions by any trained emergency personnel.

As mentioned above, the prior art method for treatment of or prophylaxis of infection by pathogenic microorganisms is based on a VIG preparation produced from non-selected plasma of revaccinated volunteers. The HT-VIG embodiment of the IVIg composition produced in accordance with the invention has several advantages over the VIG currently in use:

HT-VIG is expected to be about tenfold more potent than regular VIG. In other words, HT-VIG is expected to be substantially more potent than regular VIG.

The HT-VIG developed according to the invention may be administrated in a low volume iv or im route due to its high titre and low aggregate content. Unlike the current VIG preparation that is administered by a trained medical doctor via slow iv during hospitalization, the new product can be used in field conditions by any trained emergency personnel.

The new HT-VIG can be formulated in small and easy to use pre-filled syringes or vials.

The HT-VIG can be used for the treatment of both Vaccinia vaccination adverse effects and as a prophylactic or therapeutic treatment for Smallpox in susceptible populations.

After pooling the plasma from selected individuals, the pool may be purified and/or concentrated using well known techniques for treatment of immunoglobulin solutions. Examples of such techniques are disclosed in U.S. Pat. No. 6,468,733 and Israel Patent No. 121,900, whose contents are incorporated by reference. The method disclosed in the above U.S. patent reduces the level of protein aggregates in the concentrated immunoglobulin solution and enables the final product to reach a level of 10% protein with an acceptable level of aggregates for iv administration.

For example, a method for the purification of immunoglobulins from a source solution such as Cohn Fraction II may comprise: (a) pre-treating a cation exchange resin with an acidic solution having a pH of 4.0-4.5; (b) contacting the source solution with the cation exchange resin; and (c) eluting the immunoglobulins bound to the cation exchange resin. Prior to contact with the cation exchange resin, the source solution may be treated with an organic solvent and a detergent.

Although the invention is illustrated with respect to Vaccinia virus, the invention can be practiced with respect to other pathogenic microorganisms, and especially other viruses. Examples of such microorganisms include West Nile Virus, anthrax, rabies, CMV virus, RSV virus, hepatitis B, influenza and microorganisms which secrete Botulinium and other toxins.

It is expected that an immunoglobulin composition according to the invention may be used not only to treat adverse effects of vaccination, but also as a therapeutic or prophylactic treatment in case of an infectious outbreak.

For example, in the case of smallpox, due to the risks involved in smallpox vaccination, a significant proportion of the population would be excluded from any mass vaccination program, including all children under two years of age, pregnant and breastfeeding women, people with weakened immune systems, like primary or secondary immunodeficiency patients, and more.

In all of the above cases, the need for passive immunization would be critical during a Smallpox outbreak. Treatment with an immunoglobulin composition according to the invention could therefore be indicated for passive prophylactic immunization in this population. Alternatively, an immunoglobulin composition could be administered concomitantly with vaccination to minimise the risk of complications in these subpopulations.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

A. Preparation of an Immunoglobulin Composition

Figure 1:
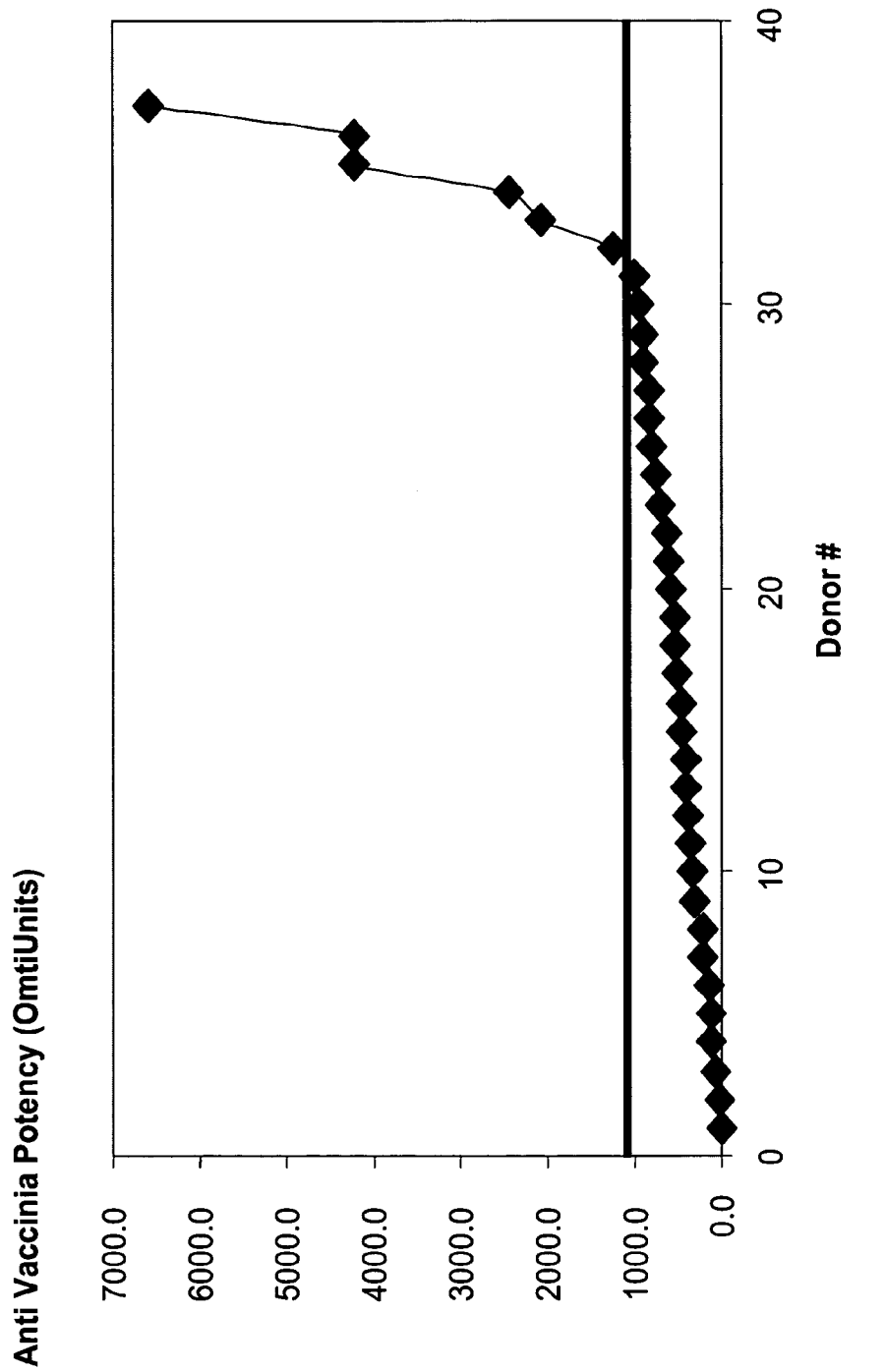
FIG. 1 is a graph showing distribution of anti-Vaccinia titers of freshly (30 days) re-vaccinated plasma donors.

One embodiment of the preparation of an immunoglobulin composition according to the invention is detailed below.

1) Establishment of Screening Tools a. Development of an ELISA Method.

A linear, competitive ELISA assay has been developed for determining vaccinia antibody titre. This assay has 2 purposes:

1. Screening of the high titer plasma donations;
2. Eventual use as a post-vaccination assessment tool.

The ELISA is relatively quick and involves relatively few reagents. Like all blood banking ELISA's, the ELISA can be performed on a single dilution with only one replicate.

Principle of the Test

Vaccinia inactivated antigen is bound to the surface of microtiter wells. Samples suspected of containing the specific immunoglobulin G (Vaccinia antibodies) such as serum, plasma, purified and concentrated immunoglobulins, calibration standards or controls are pipetted into the wells and incubated at 37° C. Vaccinia antibodies, if present, bind to the immobilized antigen. Unbound material is removed in a washing step. In a second step, a goat anti-human IgG Alkaline phosphatase conjugate is added into the wells and the ELISA plate is incubated at 37° C. After incubation, unbound conjugate is removed by washing. The enzymatic activity of alkaline phosphatase is then measured by its reaction with p-nitrophenyl phosphate substrate. The measurement is done in an ELISA reader at 405 nm. A direct relation exists between the observed optical density and the Vaccinia antibody titer.

Handling of Specimens

Blood collection should be performed according to the current practices. Serum or plasma should be separated as soon as possible to avoid any haemolysis. Specimens may be stored for 7 days at 2-8° C. before using. For longer storage, freeze specimens at −20° C. or colder.

Avoid repeated freezing and thawing. Specimens with observable particulates, or after samples have thawed, should be centrifuged prior testing.

Washing Solution Preparation

A day prior to the beginning of the ELISA procedure, prepare a working solution, by adding the entire contents of a 50 ml wash concentrate bottle (R1) to 450 ml of distilled water and mixing overnight at room temperature until complete dissolution. Prepared wash solution may be stored at 2-8° C. for up to 1 month. Prepare 500 ml for one plate of 12 strips.

Test Procedure

Sample and Standards Dilution

Using suitable test tubes and a microtiter plate, dilute the samples and standard controls as follows:

a. Test samples: First, make an initial dilution of 1:100 (10 µl sample in 990 µl sample diluent R2). Then, further dilute the samples to 1:300 (150 µl of the 1:100 dilution into 300 µl sample diluent R2) and 1:1200 (100 µl of the 1:300 dilution in 300 µl Sample Diluent R2).

b. Standard Calibrator (R3) should be diluted 1:700, 1:1000, 1:1500, 1:3000 and 1:6000 in Sample Diluent R2. Use an initial dilution of 1:100 (10 µl calibrator in 990 µl diluent R2) and then dilute further to reach the above dilutions (50 µl in 30 µl, 50 µl in 450 µl, 50 µl in 700 µl, 50 µl in 1450 µl and 50 µl in 2950 µl Sample Diluent R2, respectively).

c. Standard Negative Control (R4) should be diluted 1:300: 10 µl in 2.99 ml Sample Diluent R2.

d. Positive Control (R9) should be diluted 1:500:10 µl of R9 in 4.99 ml Sample Diluent R2.

ELISA Test Procedure

1. Pipette 100 µl of pre-diluted samples, standard calibrator (Calibrator), negative control (NegCont) and positive control (PosCont) into their respective microwells of the assay strips according to the scheme below. The Standard Calibrators should be added in duplicates. Add 100 µl of Sample Diluent (R2) into 2 wells to be used as Blanks.

| 1 | 2 | 3 | 4 |
|---|---|---|---|
| Calibrator 1:700 | Calibrator 1:700 | Sample1 1:300 | Sample1 1:1200 |
| Calibrator 1:1000 | Calibrator 1:1000 | Sample2 1:300 | Sample2 1:1200 |
| Calibrator 1:1500 | Calibrator 1:1500 | Sample3 1:300 | Sample3 1:1200 |
| Calibrator 1:3000 | Calibrator 1:3000 | Sample4 1:300 | Sample4 1:1200 |
| Calibrator 1:6000 | Calibrator 1:6000 | Sample5 1:300 | Sample5 1:1200 |
| Neg Cont 1:300 | Neg Cont 1:300 | Sample6 1:300 | Sample6 1:1200 |
| Blank | Blank | Sample7 1:300 | Sample7 1:1200 |
| Pos Cont 1:500 | Pos Cont 1:500 | Sample8 1:300 | Sample8 1:1200 |

2. Cover the strips with the plastic cover, and incubate at 37° C. for 1 hour.
3. During incubation, prepare the conjugate solution by diluting the concentrated conjugate (R6) 1:14 in the Conjugate Diluent (R5). Dilute the conjugate according to the number of strips in use: For one strip: 70 µl in 930 µl diluent; For two strips: 140 µl in 1860 µl diluent; For three strips: 215 µl in 2800 µl diluent.
4. At the end of incubation, remove the adhesive film, and using an automated plate washer, empty all wells by aspiration and wash six times (200 µl/well) with diluted wash solution. On completion of washes, ensure that all wash solution is removed.
5. Dispense into each well 100 µl of the conjugate solution. Cover the strips (see step 2), and incubate at 37° C. for 1 hour.
6. At the end of the incubation, aspirate the content of the wells and wash as described in step 4.
7. Quickly dispense into each well 100 µl of substrate solution. Cover the strips with aluminum foil and incubate for 45 minutes at room temperature.
8. Stop reaction by adding 50 µl Stop Solution (R8) to each well.
9. Carefully wipe the plate bottom. Read the absorbance (OD) of the wells at 405 nm using an ELISA microplate reader within 15 minutes of stopping the reaction.

Note: Shake the strips well before reading.

Calculation and Interpretation of the Results

1. Calculate the mean OD value for all replicates and subtract the mean Blank OD reading from all the results. For the test to be valid the following conditions should be true: (a) the mean negative control reading should be lower than the reading of the 1:700 dilution of the standard calibrator; (b) the mean negative control reading should be lower than the reading of the 1:500 dilution of the positive control.

2. Plot the net OD values at 405 nm obtained for the dilutions of the standard calibrator (on the Y-axis) against the concentrations of these dilutions in OmriU/ml (on the X-axis), where: the 1:700 dilution corresponds to 2.1 OmriU/ml; the 1:1000 dilution corresponds to 1.5 OmriU/ml; the 1:1500 dilution corresponds to 1.0 OmriU/ml; the 1:3000 dilution corresponds to 0.5 OmriU/ml; and the 1:6000 dilution corresponds to 0.25 OmriU/ml. The linear range should be 0.3-1.5 OmriU/ml.
3. Determine the Vaccinia antibody titer of the test samples by interpolation from the calibration curve, and multiplying that value by the dilution factor of the sample.
4. Determine the titer of the positive control (R9) according to the above. The whole test procedure is valid only if the titer of R9 is between 400 and 600 OmriU/ml.

Interpretation of Results

A Vaccinia immunized subject may be classified in one of the four following categories:

Very low responder: <90 OmriU/ml
Low responder: 90-440 OmriU/ml
Medium responder: 450-1800 OmriU/ml
High responder (hyper immune): >1800 OmriU/ml Accordingly and alternatively, results can be interpreted employing the table below:

| For sample dilution | For the titer of the sample determined from the calibration curve of (in OmriU/ml): | | | |
|---|---|---|---|---|
| 1:300 | <0.3 | 0.3-1.5 | >1.5 | >1.5 |
| 1:1200 | <0.3 | <0.3 | 0.3-1.5 | >1.5 |
| Response can be classified as: | Very Low <90 OmriU/ml | Low 90-440 OmriU/ml | Medium 450-1800 OmriU/ml | High >1800 OmriU/ml |

Note:
a. In most cases, only one of the two dilutions will result in a value within the linear range (0.3-1.5 OmriU/ml). However, in case both dilutions will result in a value within the linear range, the sample should be considered a low responder.
b. The classification of the vaccine response categories is tentative and is based on the Israeli vaccination program. However, a population may react differently in other vaccination programs and/or with a different vaccine preparation. Therefore, the final scheme of interpretation will be determined following the clinical study.

REFERENCES

1. Centers for Disease Control and Prevention. Vaccina (smallpox) vaccine: recommendations of the Advisory Committee on Immunization Practices (ACIP), 2001. MMWR Recomm Rep 2001 Jun. 22; 50(RR-10):1-25.
2. Frey S. E., Newman F. K., Yan L., Belshe R. B. (2003) Response to Smallpox Vaccine in persons immunized in the distant past. JAMA 289(24):3295-3299.
3. Henderson D. A. (1999) Smallpox: clinical and epidemiologic features. Emerg. Infect. Dis. 5:537-539.
4. Henderson D. A. et. al. (1999) Smallpox as a Biological Weapon. JAMA 281(22):2121-2137.
5. WHO (2001) Smallpox. Weekly Epidemiological Record 76(44): 337-344.
6. WHO Recommendations for Production and Control of Smallpox Vaccine (2004). WHO Expert Committee on Biological Standardization 53$^{rd}$ Meeting, 17-21 Feb. 2003. Final Report.

The ELISA allows for a linear continuous quantification of anti Vaccinia by generating a direct relationship between the observed optical density at 405 nm and the Vaccinia antibodies concentration in plasma and serum. 1 ml of pooled plasma derived from 50 vaccinated donors is used as a positive standard and is assigned a value of 1000 arbitrary units (=1000 OmriUnits), as described below in Example I.

2) Validation of an Anti-Vaccinia Antibody Test Kit was Performed as Follows:
   1. In house testing of accelerated stability, precision, sensitivity, specificity and recovery with negative, positive, standard and blood bank specimens. This was carried out with at least three production lots of the product (diagnostic kit).
   2. Suitable blood banks were contracted to run field validation tests. Production lot kits were supplied to those establishments and in-house training of test kit operation was provided. The blood bank was required to test sets of standard and pre-tested specimens (both negative and positive) in order to validate that the test kits are properly operated.
   3. Upon satisfactory accomplishment of (2) above, each blood bank was required to test 150 randomly selected donor specimens. Those specimens were tested in parallel with a reference test kit. If the test results from the diagnostic company test kit and the reference test were concordant, the kit was approved for routine testing of donor blood units.

3) Equivalence with the Serum Neutralization Method

The golden standard for measuring biological activity (viral inactivation) of anti-viral antibodies is the viral neutralization assay. Neutralization of a virus is defined as the loss of infectivity through reaction of the virus with a specific antibody. The loss of infectivity is brought about by interference of the bound antibody with any one of the steps leading to the release of the viral genome into the host cells.

In this assay, a constant predetermined dose of virus (400-600 PFU/ml) is allowed to react with various dilutions of the neutralizing sample (plasma or intravenous immunoglobulin) and then inoculated into cell culture.

The Plaque Reduction Neutralization Titer 50% ($PRNT_{50}$) is a specific and sensitive test that quantifies the sample dilution that gives 50% reduction in plaques relative to the virus control well. It is based on the fact that vaccinia virus produces cytopathic effects (CPE), which can be observed as plaques in BS-C-1 cell culture. This CPE is neutralized by the presence of specific antibodies.

In this assay, a given viral load is mixed with a dilution series of plasma or serum samples for a given time, after which the dilution series is then plated on the virus's host tissue culture cell line. After 48-72 hours the number of viral plaques is counted. The geometric average of the plaque number is calculated from the dilution series, as is the viral count of the control plasma without the specific antibodies. Virus counts without the control result in a number that is called Neutralization Inhibition 50—the plasma or serum dilution that gives a 50% reduction in the viral titer.

The assay is very cumbersome, takes at least 4 working days and is not adapted to high throughput samples. It involves a fully equipped virological lab with the capabilities of continuous culturing of viruses and cell culture in a highly classified control environment. Thus, the equipment, the environment and the technical skill are far above what can be found in conventional blood banking.

INSTRUMENTS AND MATERIALS

1. Instruments 1.1 1, 2, 5, 10 and 20 ml pipettes, sterile, for cell culture
1.2 6-well tissue culture plates
1.3 Flasks 75 cm$^2$
1.4 37° C. Water-jacketed Incubator with 5% $CO_2$ (OMRIX #00-020323-02)
1.5 Filter system, 0.22 μm cellulose acetate 1.6 Pump
1.7 Laminar flow hood (OMRIX #00-04030101-04)
1.8 Filter 0.8/0.2 µm, 32 mm diameter, Supor (Gelman, product #4658)
1.9 Microscope (OMRIX #00-020344-01)
1.10 37° C. water bath
1.11 Plastic tubes
1.12 Vortex
1.13 Chemical hood.
1.14 37° C. incubator (OMRIX #00-020318-03)
1.15 Folder Filter
1.16 Gauze Pad 2. Reagents 2.1 Growth medium: MEM—Earle's, without L-Glutamine (Minimum Essential Medium Eagle, Biological Industries Beit Haemek, cat. #01-025-1)
2.2 Foetal Calf Serum (FCS) (Biological Industries Beit Haemek, cat. #04-121-1)
2.3 L-Glutamine in saline, 20 millimoles (Biological Industries Beit Haemek, cat. #03-020-1)
2.4 Penicillin (10000 u/ml)-Streptomycin (10 mg/ml) Amphoteric in B (25 µg/ml) Solution (Biological Industries Beit Haemek, cat. #03-033-1)
2.5 Sodium Bicarbonate 7.5% Solution (Biological Industries Beit Haemek, cat. #03-040-1)
2.6 Nonessential Amino Acids Solution (Biological Industries Beit Haemek, cat. #01-340-1)
2.7 Sodium Pyruvate Solution 100 mM, (Biological Industries Beit Haemek, cat. #03-042-1)
2.8 Trypsin EDTA Solution (0.25% Trypsin) (Biological Industries Beit Haemek, cat. #03-050-1)
2.9 Dimethyl Sulfoxide (DMSO) (Sigma, cat. # D2650)
2.10 Tragacanth gum (Sigma, cat. # G-1128)
2.11 Ethanol (Riedel de Haen, cat. #32221)
2.12 Fuchsin Basic, Pararosaniline (Sigma, cat. # P1528)
2.13 Phenol (Sigma, cat. # P-4557)
2.14 Growth medium: MEM (Earle's) 2×, without L-Glutamine (Minimum Essential Medium Eagle, Biological Industries Beit Haemek, cat. #01-025-9)

3. Cells and Virus

BS-C-1 cells: (ATCC—CCL-26) Continuous cell line of *Cercopithecus aethiops* (monkey, African green) kidney epithelial, ATCC Lot#1182351. The cells are maintained according to SOP #08030105.

Vaccinia (IHD strain): (ATCC VR-156): Vaccinia belongs to the poxvirus family, orthopoxvirus genus. Virions enveloped; slightly pleomorphic; ovoid, or brick-shaped; 140-260 nm in diameter; 220-450 nm long. Composed of an external coat containing lipid and tubular or globular protein structures enclosing one or two lateral bodies and a core, which contains the genome. Virions contain one molecule of linear double stranded DNA 4. Preparation of Solutions 4.1 Dilution Medium—MEME, 2% FCS The medium is made up with MEM with the addition of 2 mM L-Glutamine, 1 mM sodium pyruvate, 0.1 mM Nonessential Amino Acids, 1.5 g/l sodium bicarbonate, 1% Penicillin-Streptomycin-Amphotericin B Solution, and 2% FCS. Work under sterile conditions. Add to 230 ml of MEM, 2.5 ml L-Glutamine, 2.5 ml sodium pyruvate, 2.5 ml Nonessential Amino Acids, 5 ml sodium bicarbonate, 2.5 ml Penicillin-Streptomycin-Amphotericin B Solution and 5 ml FCS respectively. Filter through a 250 ml 0.2 m cellulose acetate filter system. The medium is stable for one month at 2-8° C. if not contaminated. Before addition of medium to the cells, bring the medium to 37° C. using a water bath.

4.2 Overlay Medium—MEME 2×, 4% FCS

The medium is made up with MEM 2× with the addition of 4 mM L-Glutamine, 1% Penicillin-Streptomycin-Amphotericin B Solution, and 4% FCS. Work under sterile conditions. Add to 230 ml of MEM 2×, 5 ml L-Glutamine, 2.5 ml Penicillin-Streptomycin-Amphotericin B Solution and 10 ml FCS respectively. Filter through a 250 ml 0.2 m cellulose acetate filter system. The medium is stable for one month at 2-8° C. if not contaminated. Before addition of medium to the cells, add 2.4% sodium bicarbonate and bring the medium to 37° C. using a water bath.

4.3 Overlay Medium—Tragacanth 4.3.1 Cleaning Tragacanth

To a beaker with 60 ml EtOH, transfer 20 g tragacanth. Stir the tragacanth until reaching a homogeneous suspension (15 min) Wait until decantation and discard the supernatant Repeat the stirring 3 times. Dry the tragacanth cake using a folded filter and then by placing into a 37° C. incubator for 3 h. Pass through a gauze pad. Store at RT.

4.3.2 Working Tragacanth Medium

Dissolve 8 g clean tragacanth in 1000 ml purified water for 2 hrs at 70° C. Bring final volume to 1000 ml with purified water, then autoclave at 120° C. for 30 min. The tragacanth solution should be aliquoted to 50 ml vials under sterile condition. Store for up to two years at 2-8° C.

4.4 Staining Solution—Fuchsin

Prepare 5% Phenol by adding 50 ml Phenol to 950 ml purified water. Prepare a 3% Fuchsin solution by dissolving 3 g of Fuchsin in 100 ml EtOH. Mix well between the 100 ml Fuchsin and the 1 L Phenol solutions. Store at RT for up to 2 years. Protect from light with aluminum foil.

5. Method

The duration of a neutralization assay is 5 days, and is made up of the following stages:

Day 1: Seeding BS-C-1 cells, that were grown as described in SOP #08030105, onto a 6-well plate (section 9.1).

Day 2: Virus neutralization assay (section 9.2).

Day 5: Cell staining and determination of $PRNT_{50}$ (section 9.3)

5.1 Seeding BS-C-1 Cells (Day 1)

Seed BS-C-1 cells (passage 4-40) on a 6-well plate at a concentration of $4\times10^5$ cell/well (according to SOP #08030105). The cells should reach confluence on the next day for the virus neutralization assay (day 2).

5.2 Virus Neutralization Assay (Day 2)

5.2.1 Sample Preparations 5.2.1.1 Prepare a pool of vaccinia virus in growth medium, MEME 2% FCS, to a final concentration between 800-1200 pfu/ml.

5.2.1.2 Prepare serial dilutions of sample in growth medium, MEME 2% FCS, in the range of 1/40-1/40960. Plasma and serum samples should be inactivated at 56° C. for 30 min.

5.2.1.3 Mix each IVIG dilution with an equal volume of the vaccinia pool, thus obtaining a final dilution of 1/80-1/81920 for IVIg and a final concentration of 400-600 pfu/ml for vaccinia virus pool (e.g 500 μl of 1/40-diluted IVIg with 500 μl of 800-1200 pfu/ml vaccinia virus gives a final IVIg dilution of 1/80 and 400-600 pfu/ml vaccinia).

5.2.2 Control Preparations

Virus control: Vaccinia virus pool diluted with culture medium 1:1.

Negative Controls (no plaque reduction):

Medium control: Growth medium, MEME 2% FCS

IVIg (for IVIg assay): Mix OmriGam 5% batch # F18132 (manufactured from an American source plasma) at a dilution of 1/40 with an equal volume of the vaccinia virus pool, thus obtaining a final dilution of 1/80 for OmriGam 5% and a final concentration of 400-600 pfu/ml for the vaccinia virus pool.

Plasma (for plasma assay): Mix a negative plasma lot #3562515 (18201) at a dilution of 1/40 with an equal volume of the vaccinia virus pool, thus obtaining a final dilution of 1/80 for plasma and a final concentration of 400-600 pfu/ml for the vaccinia virus pool.

Serum (for serum assay): Mix a negative serum at a dilution of 1/40 with an equal volume of the vaccinia virus pool, thus obtaining a final dilution of 1/80 for serum and a final concentration of 400-600 pfu/ml for the vaccinia virus pool.

Positive Control (Plaque Reduction):

Mix a positive sample (H04021) at a dilution of 1/40 with an equal volume of the vaccinia virus pool, thus obtaining a final dilution of 1/80 for the positive sample and a final concentration of 400-600 pfu/ml for the vaccinia virus pool.

Roll all IVIg Mixtures and Controls for 90 Min at 37° C.

5.2.3 Virus Inoculation (Day 2)

5.2.3.1 After 90 min incubation, observe the BS-C-1 cell monolayers (that were prepared on day 1) which must be healthy and confluent.

5.2.3.2 Discard the medium from each well.

5.2.3.3 Carefully add 0.2 ml sample mixtures and controls to the wells and gently rock the plate to achieve an even distribution of the inoculums.

5.2.3.4 Allow the non-neutralized vaccinia virus to adsorb for 60 min at 37° C. in the $CO_2$ incubator.

5.2.3.5 Combine between the growth medium (MEM×2 4% FCS) and the tragacanth solution (1:1), and add 2.4% sodium bicarbonate.

5.2.3.6 Add 3 ml of the tragacanth-medium, to each well.

5.2.3.7 Incubate the plate in a 37° C. incubator for 72 hrs.

5.3 Cell Staining and Determination of $PRNT_{50}$ (Day 5)

5.3.1 Examine the plate by a microscope for observation of lysed cells.

5.3.2 The staining process should no longer be sterile. It should be carried out in a chemical hood.

5.3.3 Empty the wells by tapping.

5.3.4 Add 500 μl EtOH to each well. Wait 2 minutes. Take the solution out of the wells by tapping.

5.3.5 Add 500 μl Fuchsin staining solution (Section 8.4) to each well. Wait 2 minutes. Take the solution out of the wells by tapping.

5.3.6 Count the number of plaques.

6. Test Acceptance Criteria

Virus control should result in 80-120 PFU/well.

Negative control should result in a uniform and intact monolayer.

Plasma, serum and IVIg negative controls should give 80% plaques of the virus control.

Positive control should give a 50% plaques compared to the plasma, serum or IVIg negative control.

7. Evaluation of Results

The $PRNT_{50}$ (expressed in μg/ml) for each sample is the IgG concentration at which there is 50% neutralization of vaccinia virus as determined by the non-linear relationship (dose-response curve) between the log of the IgG concentration (initial IgG concentration divided by the dilution) and the percentage of plaque neutralization relative to the control sample (taken as 100%).

8. Reference

Virology Methods Manual, Brian W J Mahy and Hillar O Kangro.

4) Pilot Study

A pilot study was conducted with the Israel Defense Forces (IDF), which served as a model for the vaccination and screening of plasma donors. Upon a full analysis of the data, the statistical power was generated from which the exception and the exclusion criteria of the plasma donation, apart from the general blood banking, were finally formulated. The vaccination of the IDF subjects was conducted in accordance with the CDC guidelines (see the website beginning with www and followed by:bt.cdc.gov/agent/smallpox/response-plan/index.asp#guideb). Additional criteria that may arise from the full analysis of the pilot study were implemented in the vaccination protocol. Plasma screening was performed using the same standards as in the pilot study, with a few changes that were derived from the full statistical analysis of the data.

The final cutoff for high titre (HT) hyper immune donation was used after the full assessment of the titer variability and the estimation of the percentage of the population that would contribute to the HT hyper immune plasma. An example of donor variability is seen in FIG. 1. This HT hyper immune population was kept between 10-15% of all subjects who showed either sero-conversion or clinical signs that the immunization was successful. Plasma collection was conducted according to the FDA guidelines and the local blood banks' standard operation. Selected subjects was repeatedly taken advantage of, for example by using a plasmapheresis or plasma donation technique (see for example U.S. Pat. No. 6,692,739, whose contents are incorporated herein by reference).

Subjects without any clinical signs were excluded from plasma donation. These subjects were revaccinated. Clinical signs are as follows:

A normal primary vaccination appears as a papule after 3-4 days, and rapidly progresses to a vesicle with the surrounding erythema by the 5th-6th day. The vesicle center becomes depressed and progresses to a well-formed pustule by the 8th-9th day. By the twelfth day, or soon thereafter, the pustule crusts over, forming a brown scab, which progresses from the center of the pustule to the periphery. After 2.5 to 3 weeks, the scab detaches and a well-formed scar remains.

TABLE 2

Normal Reaction Times to Vaccinia vaccination

| Day | Description |
|---|---|
| 0 | Vaccination |
| 3-4 | Papule |
| 5-6 | Vesicle with surrounding erythema → vesicle with depressed center |
| 8-9 | Well-formed pustule |
| 12+ | Pustule crusts over → scab |
| 17-21 | Scab detaches revealing scar |

Rarely, in some previously unvaccinated individuals, seemingly appropriate vaccination techniques may not result in any reaction. One should assume that the individual is not immune and repeat attempts should be made to achieve a primary take. At least three attempts should be made, switching skin sites after a second unsuccessful attempt.

Systemic symptoms: Systemic symptoms are expected and usually occur about a week after vaccination. These include:
- Soreness at the vaccination site
- Intense erythema ringing the vaccination site
- Malaise
- Lymphadenopathy (local)
- Myalgia, headache, chills, nausea, fatigue
- Fever The occurrence of these normal reactions varies considerably from study to study. The following table lists the symptoms covered by the studies and provides an indication of the range:

TABLE 3

Occurrence of reactions to Vaccinia vaccine

| Reaction | Occurrence |
| --- | --- |
| Lymphadenopathy | 25.0-50.0% |
| Myalgia, headache, chills, nausea, fatigue | 0.3-37.0% |
| Fever >37.7° C. | 2.0-16.0% |

The plasma donation should take place when the scab from the vaccine separates from the skin, or 21 days post-vaccination, whichever is later. All plasma samples were qualified according to the FDA guidelines for plasma safety. All qualified donations were screened for high Vaccinia titer. Only plasma donation with predetermined minimal Vaccinia titers will be pooled for fractionation of HT hyper immune VIG.

Receipt of plasma donation and release for fractionation was according to preset acceptance criteria. These criteria include only using plasma units with vaccinia antibodies titers above 1800 OmriUnits/ml.

Production of HT hyper immune VIG batches.

a. Re-suspension of 10-12 Kg of paste II (equivalent to 2.5-3.0 Kg of immunoglobulin).

b. Manufacturing of bulk 10% solvent detergent treated and 20 nanometer filters immunoglobulin.

c. Filling the product into 2 ml prefillable syringes.

The HT hyper immune VIG may be characterized according to the USP monograph for intramuscular immunoglobulin. Stability studies of the HT hyper immune VIG final containers should also be carried out.

The following is a product characterization of one example of an immunoglobulin composition (HT-VIG) according to the invention.

Composition

HT-VIG is a sterile solution containing 10% protein (100 mg in 1 ml solution of which at least 95% is Human Normal Immunoglobulin G), 10% maltose, and Water for Injections.

Manufacturing Process Description

HT-VIG is obtained by Cohn-cold ethanol fractionation of plasma.

Safety

HT-VIG undergoes viral removal/inactivation technology; composed of 3 viral inactivation steps: The Cohn-cold ethanol fractionation has been validated as a primary virus inactivation step. HT-VIG undergoes a second virus inactivation step by the Solvent Detergent method using TnBP/Triton X-100 and a third inactivation step by nanofiltration at pH 4 and makes HT-VIG a very safe immunoglobulin.

Pharmaceutical Form

HT-VIG is a clear or slightly opalescent, almost odourless, colourless to pale yellow liquid for intravenous or intramuscular administration.

Vial Type

The sterile filling of the product is carried out in glass, siliconized vials of 10 ml with 4-5 ml fill volume or in a pre-filled 4-5 ml syringe.

Storage Conditions

Vials/syringes should be stored at a temperature between 2-8° C., protected from light 2. Specific Information

| PARAMETERS | LIMITS |
|---|---|
| Characters | Clear or slightly opalescent and colorless or pale yellow solution. |
| Ouchterlony | Gives a positive reaction with human protein anti-sera and a negative reaction with animal protein anti-sera. |
| IgG by Cellulose Acetate Electrophoresis | ≥95% |
| IgG Content | 85 mg/ml-110 mg/ml |
| Vaccinia Antibody Titer | 40,000/OU/ml |
| Anti-Hepatitis A | >100 IU/ml |
| Anti-HBsAg | >0.5 IU/g IgG |
| Total Protein | 8.3%-1.1% (w/v) |
| Distribution of molecular size (HPLC) | Monomer and dimer ≥90.00% Polymers and aggregates ≤3.00% |
| Anticomplementary Activity | ≤1 $CH_{50}$/mg IgG* |
| Prekallicrein Activity* | ≤35 IU/ml* |
| Anti-A & Anti B Haemagglutinins | The 1:64 dilutions do not show agglutination* |
| Tri-n Butyl Phosphate (GC) | ≤5.0 μg/ml (ppm)* |
| Triton X-100 (HPLC) | ≤5.0 μg/ml (ppm)* |
| IgA content | ≤0.36 mg/ml |
| IgM content | ≤0.24 mg/ml (≤10 mg/dl) |
| pH | 5.1-6.0 |
| Osmolality | ≥240 mOsmol/kg $H_2O$ |
| Sodium (Flame Photometer) | <20 mmol/l |
| Maltose | 90-110 g/l |
| Pyrogens (10 ml/Kg Rabbit) | Non Pyrogenic |
| Sterility (Steritest) | Sterile |
| Ag HBs | Negative |
| Ab HIV | Negative |
| Ab HCV | Negative |
| HCV-RNA (PCR) in plasma pool | Negative |

B. Data Collection, Analysis & Interpretation

Data collection is a straightforward process and can follow the local data banking Standard Operating Procedures (SOP) already in place at each center.

The subjects' questionnaires for the vaccination and the evaluation of the screening program, was formulated. The blood collection, storage and shipment instruction were written and supervised according to SOP. All attachments to the vaccination screening and plasma collection protocols were formatted in an electronic copy as well as a hard copy to allow for analysis and surveillance by the Quality Assurance team. Data was entered into a PC-based database system (e.g. Paradox) to enable on-line querying and production of up to date reports.

All statistical analysis was performed using a statistical software package for the PC (e.g. SAS). Standard parametric tests were run to compare symptomatic and antibody responses. Primary analysis included safety, serological and clinical data. The parameters for response to the vaccine included data of clinical skin reactions, normal reactions, adverse effects, severe adverse effects and anti-Vaccinia titers. Those subjects having titers that are above the threshold chosen as eligible for collection and assigned for hyper immune, were included in the preliminary analysis, but they were also analyzed separately in a sub-analysis to see if they correlate to any of the parameters collected in the vaccination questionnaire.

C. Safety

Viral removal/inactivation technologies are well known. For example, one such technology is disclosed in U.S. Pat. No. 6,468,733, whose contents are incorporated herein by reference. The HT-VIG product may include viral removal steps according to these technologies, such as nano-filtration and solvent detergent treatment, which exhibit high margins of viral inactivation of all known viruses, including Parvoviruses. The solvent-detergent was removed through a specific solvent detergent removal resin that has the capability of binding hydrophobic substances and molecular sieving of large molecules. The column outflow yields an immunoglobulin solution that has a very low dimer and polymer content, allowing a high throughput through nanofiltration. This results in a liquid immunoglobulin preparation that is devoid of active viruses, while featuring a very high yield. Furthermore, the above process can be performed at a low pH thus allowing in addition the inactivation of viruses that are sensitive to low pH.

The storage of the liquid product may be at room temperature for at least two years in pre-filled, ready to use syringes. For longer storage times, the product may be stable for up to 3 years at 2-8° C.

D. Results

Three studies concerning Israeli and U.S. plasma donation samples have been conducted:

Plasma for fractionation and manufacturing of hyper immune Vaccinia immunoglobulin is usually collected from voluntarily revaccinated donors. To commence this investigation, the variability of anti Vaccinia immunoglobulin in the plasma donations and percentage of plasma units suitable for pooling was studied.

The collection of suitable plasma donations from revaccinated subjects is based on clinical manifestation of the vaccine. On the other hand the hyper immune plasma collection is based primarily on the plasma titers. The correlation between these two methods was assessed.

Manufacturing of hyper immunoglobulins carries inherent risks of achieving low yields that might drastically reduce the economic viability of certain manufacturing technology. The highly sensitive ELISA assay can detect residual titers of anti-Vaccinia IgG in regular plasma pools. It can also detect this immunoglobulin G in intravenous immunoglobulin batches. The theoretical yield of the VIG production process was calculated. The results indicated that the method of the invention is suitable for the production of High Titer VIG.

Example 1

Screening of Anti Vaccinia Titers in Plasma Units Donated by Revaccinated Subjects Background: Plasma donations for the production of Vaccinia-rich intravenous immunoglobulin were collected from revaccinated donors during the Israeli emergency program, in which selected military and health services personnel were vaccinated against Smallpox. Since donor selection was based exclusively on clinical manifestation signs and not on sero-conversion immunoglobulin titers, an assessment was needed to evaluate the titers in plasma manufacturing pools.

Methods: 37 plasma donations were selected randomly out of 24,000 subjects who were inoculated intradermally 30 days previously with 20 µl of the Elstree Vaccinia virus (mean titer, $10^7$ pfu per milliliter). The plasma units were monitored for the titers of anti-Vaccinia immunoglobulin using an ELISA assay. 3 ml of each of the plasma donations were mixed with the other samples and the pool served as a positive standard. The pooled plasma positive standard was then assigned 1000 arbitrary units (1000 OmriUnits/ml). 20-40 OmriUnits will neutralize Vaccinia virus by 50% in a neutralization assay of the kind described above (the PRNT50 assay). The pooled Vaccinia plasma positive standard may be obtained on request from OMRIX Biopharmaceuticals, Ltd., Tel Aviv, Israel.

Results: The results are summarized in FIG. 1. It was found that the variability in the donated plasma units ranged between 26 units and 6530 OmriUnits. The calculated average was 971.8 OmriUnits, the standard deviation was 1349 while the median was only 542 OmriUnits. The results of the calculated average coincides with the average of the experimentally mix plasma units, indicating that the mixture of different plasma units does not differ from the calculated one. This indicates that the ELISA does not suffer form inhibitory reactions often occurring when plasma donations are mixed.

Conclusion: Only about 10% of the population had titers that are significantly higher than the average of the plasma donation collected from revaccinated subjects. It is apparent that if only plasma donations that have titers higher than 1800 OmriUnits/ml are collected (very high titer plasma donations), the pooled hyper immune plasma titer would be at least 5 times higher than the regular rich pooled Vaccinia immunoglobulin. It is therefore obvious that screening of plasma donation of all revaccinated population is required to identify very high titre individuals having a very high titre of the specific antibodies.

Figure 2:
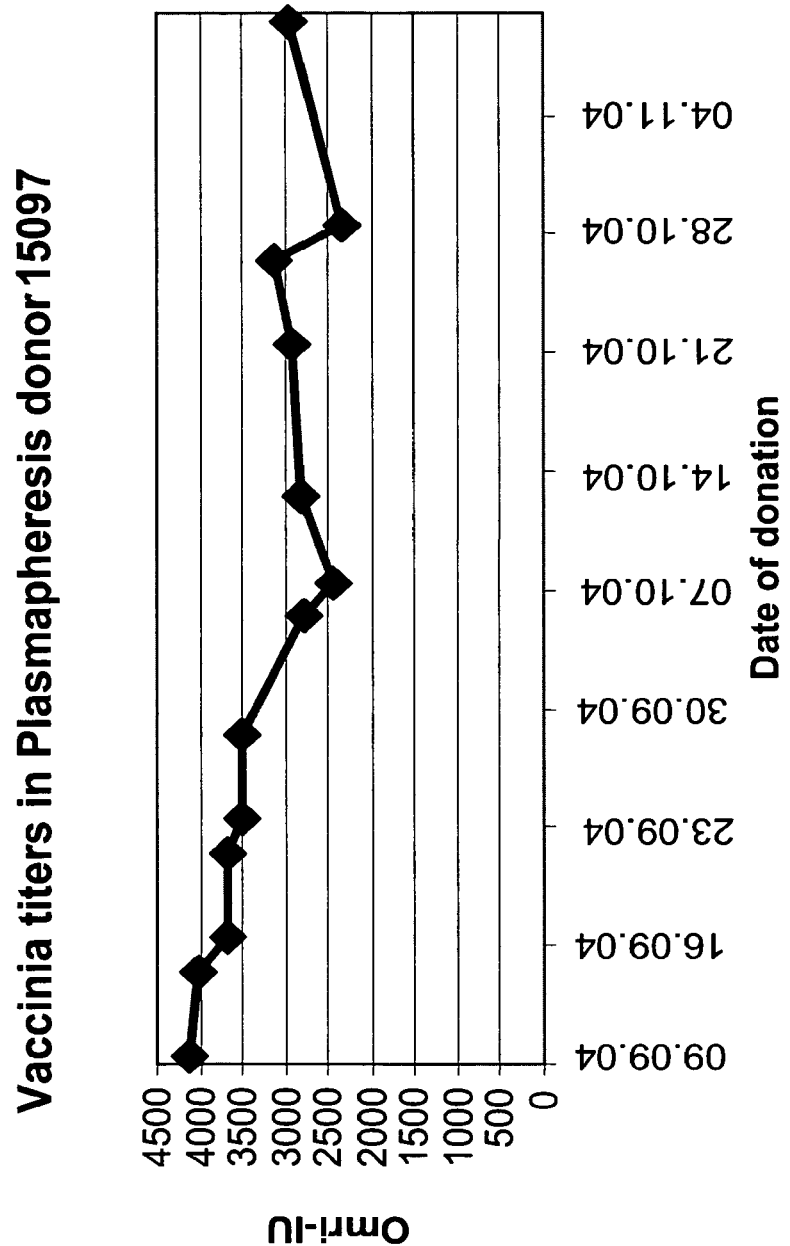
FIGS. 2 and 3 show fluctuations in the level of Vaccinia antibody titres in two high titre individuals over a period of several months.
Figure 3:
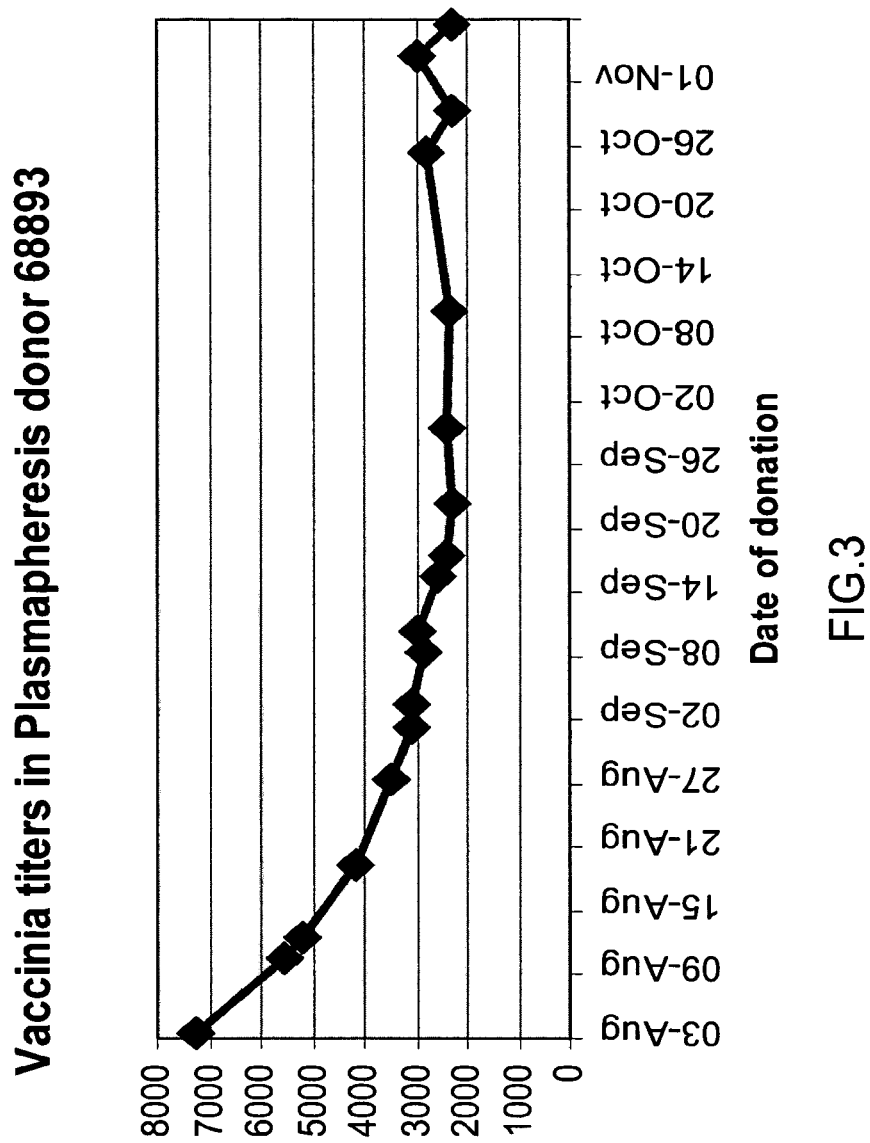

It was found that the very high titre individuals stably maintain a very high titre of specific antibodies. FIGS. 2 and 3 show the titers of two high titre individuals of about 3000 OmriUnits/ml. This titre was maintained even 3 months after revaccination and following almost 20 plasma donations.

Example 2

Correlation Between Clinical Responses and Sero-Conversion of Smallpox Vaccination of Revaccinated Adults Background: The production of Vaccinia Immune Globulin (VIG) relies on the collection of plasma from recently vaccinated adult subjects. Recent reports indicated that the clinical response of naïve subjects exceeded 95%, while reports from the early 1960s showed that the clinical response in revaccinated children is much lower. A clinical experiment was designed to evaluate the response percentage and to assess the correlation between the revaccinated subjects' clinical response and the increase in anti-Vaccinia titers.

Method: In this randomized, single-blind, prospective study, 157 adults who had been previously immunized, were inoculated intradermally with 20 µl of the Elstree Vaccinia virus (mean titer, $10^7$ pfu per milliliter), using a hypodermic needle, and the site was covered with a semi permeable dressing. Subjects were monitored for vesicle formation on days 3-4 and days 7-9 (a clinical response of the success of vaccination) and for adverse events for 30 days after immunization. Serum samples were taken on day 0 (before the vaccination), day 14, and day 30 (plasma donation). The serum titers were tested using the linear, quantitative ELISA.

Results: Success rates differed only slightly between the clinical responders and sero-conversion. Clinical responders were 62.87%—very similar to the subjects who demonstrated sero-conversion (62.42%). Serum titers in all the responding subjects were reduced by an average of 30% between the 14th and 30th days after the re-vaccination. In addition to the formation of pustules, common adverse events consistent with the presence of an acute viral illness including the formation of satellite lesions, regional lymphadenopathy, fever, headache, nausea, muscle aches, fatigue, and chills appeared only in a small percentage of the subjects.

The correlation between the sero-converted subjects (results of day 14 vs. day 0) and the clinical formation of pustules appearance on days 7-9 was 87.74%—very close to the correlation percentage found between the sero-converted subjects that have pustules on days 3-4 and/or days 7-9 (88.44).

Serum titers at day 0 were very variable, and become even more variable as titers increased after 14 days. This variability appeared also at 30 days after the vaccination. Only 10-15 percent of the subjects had high titers that would be suitable for hyper immune Vaccinia immunoglobulin production.

Conclusions: When 20 µl of Elstree vaccine strain at a titer of $10^7$ PFU is given to revaccinated adult subjects, 62.87 responded clinically, similar to the 62.42 sero-conversion rates. There is a very high correlation between the two methods (about 88%). Anti-Vaccinia titers reach a peak at 14 days after vaccination and decline by about 30% at 30 days. The titers of the revaccinated subjects was shown to be highly variable at 30 days after the vaccination and only 10-15% of the revaccinated subjects had titers above 1000 Arbitrary units which comply with the production of hyper-immune vaccine globulins. These data suggest that a screening test for the hyper-immune subject should be mandatory.

SUMMARY

Preliminary studies indicate that the titers of immunoglobulin G of revaccinated volunteers are very variable, thus VIG products that are produced from such pooled plasma result in relatively low titers. The studies indicate that it is feasible to utilize the fast screening ELISA method in which the high titer anti Vaccinia plasma samples can be singled out. Pooling high titer plasma units that account for 10-15% of the donor population for the production of a 10% intravenous immunoglobulin and concentrating the pool would result in production of HT-VIG.

The invention claimed is:
1. An immunoglobulin composition prepared according to the method comprising:
   a) selecting a population of at least 50 individuals revaccinated against one or more antigens associated with a particular pathogenic microorganism;
   b) identifying very high titre individuals from said population having a very high titre of specific antibodies immunoreactive with one or more antigens associated with said pathogenic microorganism by an immunoassay in a blood or blood component of said individuals, wherein said very high titre individuals are defined as those of the highest responders whose pooled blood or blood components have an average titre of said specific antibodies that is at least five times higher than the average titre of said specific antibodies of the pooled blood or blood components of the entire population of step (a);
   c) combining blood or blood components comprising immunoglobulins from said very high titre individuals; and
   d) purifying and/or concentrating the product of step (c), to obtain a concentrated immunoglobulin composition comprising at least 10% total protein of which at least 95% is immunoglobulin, which concentrated immunoglobulin composition has a titre significantly at least five times greater than that attainable using a pooled plasma positive standard, prepared from the entire population of step (a).

2. The immunoglobulin composition according to claim 1, having an aggregate content of less than 3% protein.

3. A vial or pre-filled syringe containing less than 10 ml of the composition according to claim 1.

4. The immunoglobulin composition according to claim 1, wherein said pathogenic microorganism is a vaccinia virus, and wherein said specific antibodies are anti-vaccinia antibodies.

5. The immunoglobulin composition according to claim 4, comprising specific anti-vaccinia antibodies at a titre of greater than or equal to 40,000 OmriUnits/ml when measured using an ELISA assay in which a pooled plasma positive standard, prepared from a population of individuals previously vaccinated against one or more antigens associated with vaccinia virus, is assigned the value of 1000 OmriUnits/ml.

* * * * *